(12) United States Patent
Roberts et al.

(10) Patent No.: US 9,604,011 B2
(45) Date of Patent: Mar. 28, 2017

(54) SAFETY DEVICE FOR A PRE-FILLED SYRINGE AND INJECTION DEVICE

(75) Inventors: Gareth Roberts, Wrexham (GB); Sioned Owen, Denbigh (GB); Matthew Ekman, Chesire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 402 days.

(21) Appl. No.: 13/977,447

(22) PCT Filed: Dec. 30, 2011

(86) PCT No.: PCT/EP2011/074280
§ 371 (c)(1),
(2), (4) Date: Jun. 28, 2013

(87) PCT Pub. No.: WO2012/093075
PCT Pub. Date: Jul. 12, 2012

(65) Prior Publication Data
US 2013/0289480 A1 Oct. 31, 2013

(30) Foreign Application Priority Data
Jan. 4, 2011 (EP) .................................... 11150083

(51) Int. Cl.
*A61M 5/32* (2006.01)
(52) U.S. Cl.
CPC ........ *A61M 5/3245* (2013.01); *A61M 5/3204* (2013.01); *A61M 5/326* (2013.01);
(Continued)
(58) Field of Classification Search
CPC .............. A61M 5/3232; A61M 5/3234; A61M 5/3257; A61M 5/326; A61M 5/3271;
(Continued)

(56) References Cited

U.S. PATENT DOCUMENTS

| 5,423,758 A * | 6/1995 | Shaw | A61B 5/1438 |
| | | | 600/576 |
| 7,300,420 B2 * | 11/2007 | Doyle | A61M 5/326 |
| | | | 604/192 |

(Continued)

FOREIGN PATENT DOCUMENTS

| FR | 2884721 A1 | 10/2006 |
| FR | 2899482 A1 | 10/2007 |

(Continued)

OTHER PUBLICATIONS

International Preliminary Report on Patentability in International Application No. PCT/EP2011/074280, dated Jul. 10, 2013, 6 pages.
(Continued)

*Primary Examiner* — Laura Bouchelle
*Assistant Examiner* — Justin L Zamory
(74) *Attorney, Agent, or Firm* — Fish & Richardson P.C.

(57) ABSTRACT

According to the invention, a safety device for a pre-filled syringe comprises
  a hollow support body for retaining the pre-filled syringe,
  a hollow needle shield that is movable relative to the support body from a first position to a second position,
  releasable mounting means to mount the pre-filled syringe within the support body and
  a spring means arranged within the support body in a non-energized or only slightly energized state.
The movement of the needle shield from the first position to the second position fully energizes the spring means.

20 Claims, 7 Drawing Sheets

(52) U.S. Cl.
CPC ......... *A61M 5/3257* (2013.01); *A61M 5/3287* (2013.01); *A61M 2005/3267* (2013.01)

(58) Field of Classification Search
CPC .. A61M 2005/3264; A61M 2005/3267; A61M 2005/3235; A61M 2005/3239; A61M 2005/3236; A61M 2005/3234
See application file for complete search history.

(56) References Cited

U.S. PATENT DOCUMENTS

| | | | |
|---|---|---|---|
| 7,361,160 | B2 | 4/2008 | Hommann et al. |
| 7,976,499 | B2 | 7/2011 | Grunhut et al. |
| 8,308,687 | B2 | 11/2012 | Carrel et al. |
| 2003/0004468 | A1* | 1/2003 | Righi et al. ............ 604/243 |
| 2005/0273061 | A1 | 12/2005 | Hommann et al. |
| 2005/0277894 | A1* | 12/2005 | Westbye et al. ......... 604/198 |
| 2009/0024093 | A1 | 1/2009 | Carrel et al. |
| 2009/0312705 | A1 | 12/2009 | Grunhut et al. |
| 2009/0318864 | A1* | 12/2009 | Carrel et al. .......... 604/117 |
| 2010/0042053 | A1* | 2/2010 | Dillard, III ....... A61M 5/3257 604/198 |
| 2010/0292653 | A1* | 11/2010 | Maritan .............. 604/198 |

FOREIGN PATENT DOCUMENTS

| | | |
|---|---|---|
| JP | 2008/220934 | 9/2008 |
| JP | 2009/533124 | 9/2009 |
| WO | 2004047892 A1 | 6/2004 |
| WO | 2005113039 A1 | 12/2005 |
| WO | 2007026163 A1 | 3/2007 |
| WO | 2009040607 A1 | 4/2009 |
| WO | 2010076569 A2 | 7/2010 |

OTHER PUBLICATIONS

International Search Report and Written Opinion in International Application No. PCT/EP2011/074280, mailed Feb. 23, 2012, 9 pages.

Rote Liste, "50. Hypophysen-, Hypothalamushormone, andere regulatorische Peptide u. ihre Hemmstoffe," Chapter 50, ed. 2008, 20 pages.

* cited by examiner

SAFETY DEVICE FOR A PRE-FILLED SYRINGE AND INJECTION DEVICE

CROSS REFERENCE TO RELATED APPLICATIONS

The present application is a U.S. National Phase Application pursuant to 35 U.S.C. §371 of International Application No. PCT/EP2011/074280 filed Dec. 30, 2011, which claims priority to European Patent Application No. 11150083.1 filed Jan. 4, 2011. The entire disclosure contents of these applications are herewith incorporated by reference into the present application.

FIELD OF INVENTION

The present invention relates to safety devices that provide needle safety and more particularly to safety devices for pre-filled syringes. The safety device is adapted to avoid accidental needle pricks and needle injuries before, during and after an injection of a medication or drug contained in the pre-filled syringe. In particular, the safety device provides needle safety for a subcutaneous self-administrated injection or for an injection administered by a health-care professional. The present invention further relates to injection devices comprising a pre-filled syringe.

BACKGROUND

Pre-filled syringes that are filled with a selected dosage of a medication are well known injection devices for administering the medication to a patient. Safety devices for covering a needle of a pre-filled syringe before and after use are also well known. Typically, these devices comprise a needle shield that is either manually moved or moved by the action of a relaxing spring to surround the needle.

A different type of safety device known in the state of the art achieves the object of providing needle safety by arranging the pre-filled syringe movable relative to a body, where the pre-filled syringe is retracted into the body after the injection.

SUMMARY

It is an object of the present invention to provide an improved safety device for a pre-filled syringe.

It is a further object of the invention to provide an improved injection device comprising a pre-filled syringe that is safe to handle and in particular prevents accidental needle stick injuries.

The object is achieved by a safety device according to claim 1 and by an injection device according to claim 12.

Preferred embodiments of the invention are given in the dependent claims.

In the context of this specification, the terms distal and proximal are defined from the point of view of a person performing an injection. Consequently, a distal direction refers to a direction pointing towards the body of a patient receiving an injection and a distal end defines an end of an element that is directed towards the body of the patient. Respectively, the proximal end of an element or the proximal direction is directed away from the body of the patient receiving the injection and opposite to the distal end or distal direction.

According to the invention, a safety device for a pre-filled syringe comprises
a hollow support body for retaining the pre-filled syringe,
a hollow needle shield that is movable relative to the support body from a first position to a second position,
releasable mounting means to mount the pre-filled syringe within the support body and
a spring means arranged within the support body in a non-energized or only slightly energized state. The movement of the needle shield from the first to the second position fully energizes the spring means.

The needle shield in the first position of the safety device surrounds a hypodermic needle of the pre-filled syringe prior the injection, so that accidental needle stick injuries are prevented. Before the hypodermic needle is inserted into the skin of a patient, the needle shield is moved proximally from the first position towards the second position, whereby the initially non-energized or only slightly energized spring means is charged. When the needle shield reaches the second position, the spring means is fully charged, so that the pre-filled syringe may be retracted by the action of the relaxing spring means. The spring means is thus charged during the use of the safety device. As the spring means is arranged within the safety device in the non-energized or slightly energized state, material fatigue is avoided. Thus, the shelf-life of the safety device is extended, so that the safety device works reliably even after extended periods of storage.

Furthermore, the safety device comprises only a few parts preferably made from plastics material to ensure needle safety. The safety device may thus be economically produced in large quantities and is suited to be used in combination of disposable pre-filled syringes.

The needle shield of the safety device may move proximally from the first to the second position, whereas a movement of the needle shield from the second position to the first position is prevented by a locking means. As the proximal movement of the needle shield charges the spring means, so that the mounting means may be released and the pre-filled syringe may be retracted after the injection, the restriction of the needle shield's movement by the locking means effectively provides a means that prevents a re-use of the device. In particular, inadvertent contact with a used and contaminated hypodermic needle is thus prevented.

According to a possible embodiment of the invention, the needle shield comprises at least one locking catch that protrudes into a first recess formed into the support body to retain the needle shield in the first position. The needle shield is releasably retained in the first position by the locking catch engaging the first recess. The locking catch has a shape that allows for a proximal movement of the needle shield, whereas a distal movement of the needle shield with respect to the support body is prevented.

The locking catch may latch to a second recess formed into the support body to irreversibly lock the needle shield to the second position. The needle shield is thus firmly retained in the second position. The needle shield in the second position acts as a bearing surface of the fully energized spring means. The irreversible locking of the needle shield thus ensures that the spring means may exert a sufficient biasing force upon the pre-filled syringe, so that the pre-filled syringe may be retracted within the support body after the injection has been performed.

According to a possible embodiment of the invention, the safety device generates a first audible feedback when the needle shield reaches the second position, wherein the spring means is fully energized. The hypodermic needle projects from the safety device in the distal direction by a length that corresponds to a penetration depth of the hypodermic needle when the needle shield is in the second position. The user of the safety device thus advised to proceed with the injection by the second audible feedback.

In one possible embodiment of the invention, the spring means is a conventional compression spring made from a metal.

Alternatively, the spring means may be made from a plastics material like a polymer or an elastomer. In this alternative embodiment, the safety device is completely made from inexpensive plastics materials. The safety device may thus be cost-efficiently produced in large quantities.

According to a possible embodiment of the invention, an outer body is slideably arranged relative to the support body. The outer body substantially receives the support body at the end of an injection stroke, whereby the outer body releases the mounting means. The outer body moves with respect to the support body in a linear translatory motion to dispose a medication contained in the pre-filled syringe beneath the skin of the patient. At the end of injection stroke, the mounting means are released by the outer body, so that the pre-filled syringe retained in the support body may be refracted within the support body. An additional interaction is not required to ensure needle safety after the injection has been carried out.

According to a possible embodiment of the invention, the safety device generates a second audible feedback that indicates the release of the mounting means. A user of the device thus knows when the medication or drug has been completely delivered and when the safety device may be safely removed from the injection site.

According to another possible embodiment, the mounting means comprise at least one clamp arm connected or integrated to the support body. The clamp arm is adapted to clamp to a collar of the pre-filled syringe. The clamp arm provides a simple releasable means to mount the pre-filled syringe within the support body of the safety device.

The outer body may comprise at least one release catch that engages a tapered flank of the clamp arm to deflect the clamp arm in a radial outward direction, whereby the mounting means are released. The release catch is located at a proximal end of the outer body, so that the clamp arm is engaged by the release catch to release the mounting means at the end of the injection stroke and after the medication has been completely disposed beneath the skin of the patient.

According to an alternative embodiment of the invention, the clamp arm is hinged to the support body. The clamp arm comprises an outward projection adapted to be engaged by an inward projection formed to an inner surface of the outer body when the support body is substantially received within the outer body at the end of the injection stroke. Engagement of the outer projection by the inward projection causes the clamp arm to pivot about a hinge, whereby the mounting means are released.

An injection device comprises a safety device and a pre-filled syringe with a hypodermic needle. The releasable mounting means mount the pre-filled syringe within the support body in an advanced position, so that the hypodermic needle protrudes the distal end of the support body. The hypodermic needle is surrounded by the needle shield in the first position and exposed in the retracted position. The injection device comprising the pre-filled syringe and the safety device combines the aforementioned advantages and avoids inadvertent needle sticks before, during and after an injection delivering the medication beneath the skin of a patient.

According to a possible embodiment of the invention, the spring means engages a collar of the pre-filled syringe to retract the pre-filled syringe with respect to the support body. An additional part to connect the spring means to the pre-filled syringe is not necessary. The safety device comprises only few parts and thus may be economically mass-produced.

The outer body releases the mounting means at the end of the injection stroke. The pre-filled syringe is moved proximally to a refracted position by the action of the relaxing spring means. The hypodermic needle of the pre-filled syringe in the retracted position is surrounded by the support body, so that accidental needle stick injuries are prevented.

The pre-filled syringe may be filled with a medicament.

The term "medication", or "drug", or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)$_5$-des Pro36, des Pro37 Exendin-4(1-39)-NH2,
des Pro36 Exendin-4(1-39),
des Pro36[Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)$_5$des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2, H-(Lys)6-des Pro36, Pro37, Pro38 [Met(O)14, Asp28] Exendin-4(1-39)-(Lys)6-NH2,
H-Asn-(Glu)$_5$ des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Details of the present invention are described hereinafter. However, it should be understood that the detailed description and the specific examples indicate possible embodiments of the invention and are given by way of illustration only. Various changes and modifications of the illustrated embodiments within the spirit and scope of the invention are appreciated by those skilled in the art.

BRIEF DESCRIPTION OF THE DRAWINGS

The present invention will be better understood from the detailed description given in the following. The accompanying drawings are given for illustrative purposes only and do not limit the scope of the present invention.

Corresponding parts are marked with the same reference symbols in all figures.

DETAILED DESCRIPTION

In the following, the term distal is used to describe a direction directed towards a skin of a patient receiving an injection. Correspondingly, the term proximal describes a direction directed away from the skin of the patient.

Figure 1:
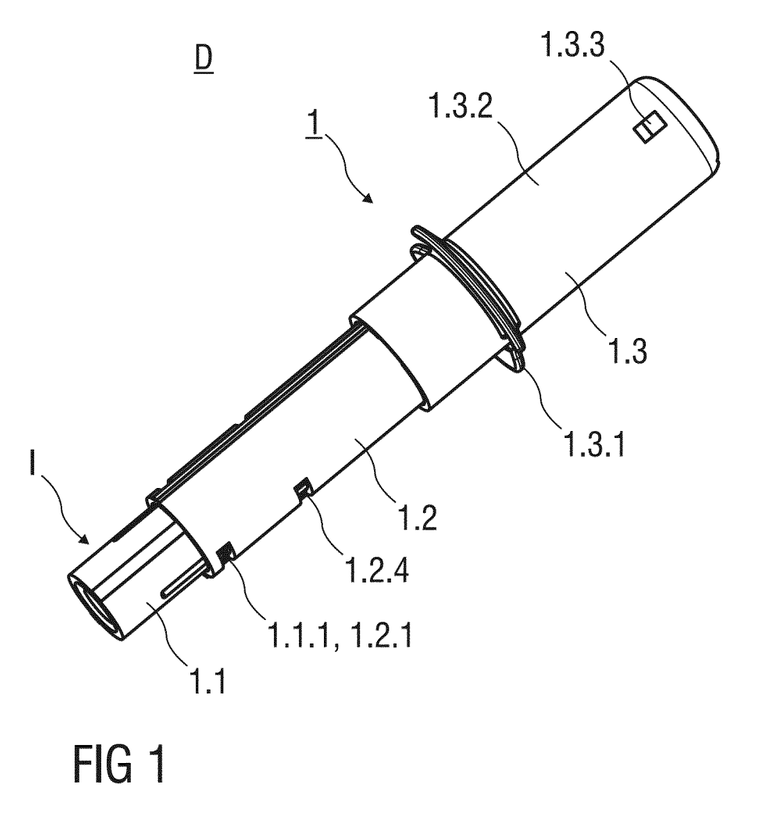
FIG. 1 shows a perspective view of an injection device before use.

FIG. 1 shows an injection device D comprising a safety device 1 and a pre-filled syringe 2 as it is delivered to an end-user. The safety device 1 comprises a hollow needle shield 1.1, a support body 1.2 and an outer body 1.3. The pre-filled syringe 2 is received inside the support body 1.2, so that a hypodermic needle 2.1 of the pre-filled syringe 2.1 protrudes distally beyond the support body 1.2. The needle shield 1.1 is inserted in an open distal end of the support shield 1.2 and arranged in an extended first position I, in which the hypodermic needle 2.1 is surrounded by the needle shield 1.1 prior to use of the safety device 1.

Additionally or alternatively, the needle shield 1.1 may comprise a surface of increased area adapted to rest on a skin surface of the patient during an injection.

The needle shield 1.1 may be made from an opaque plastics material, so that the hypodermic needle 2.1 is shed from the view of a patient of the injection device D prior an injection. This may ease a possible fear of needles of the patient. The safety device 1 is thus particularly suited for performing self-administered injections.

Alternatively, the needle shield 1.2 may be made from a transparent plastics material. A healthcare professional that uses the safety device 1 thus can visually confirm the correct placement of the hypodermic needle 2.1 penetrating the skin of the patient, even when the hypodermic needle 2.1 is surrounded by the needle shield 1.2.

As the safety device 1 is both suited for self-administered injections and injections carried out by a healthcare professional, the person referred to as the user or the patient may be one and the same person.

A circumferential hand-abutting flange 1.3.1 is moulded to an outer body 1.3 close to its distal end to allow a proximal section 1.3.2 of the outer body 1.3 to be gripped by a hand of the user performing an injection stroke.

The needle shield 1.1, the support body 1.2 and the outer body 1.3 are made from a plastics material like a polymer.

Figure 2:
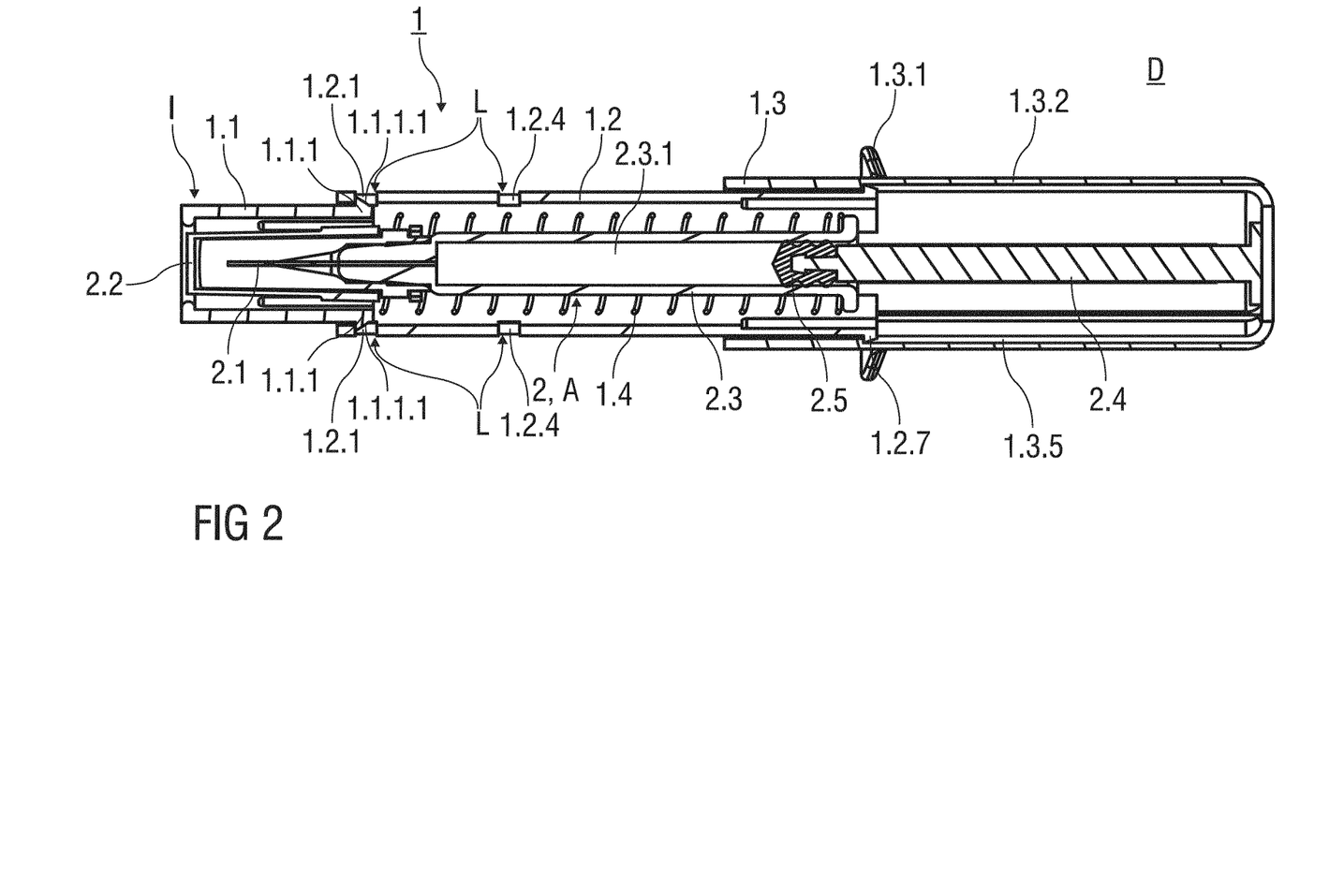
FIG. 2 shows a sectional view of the injection device according to a first cross-section prior to use.

FIG. 2 shows a sectional view of the injection device D according to a first cross-section prior to use. The pre-filled syringe 2 is retained in the support body 1.2 in an advanced position A, wherein the hypodermic needle 2.1 projects from the support body 1.2 in the distal direction. The pre-filled syringe 2 comprises a barrel 2.3 having an inner cavity 2.3.1 containing a medication. The inner cavity 2.3.1 is in fluid communication with the hypodermic needle 2.1. A needle cap 2.2 frictionally engages a distal end of the barrel 2.3 to cover the hypodermic needle 2.1 before the injection. The needle cap 2.2 is surrounded by the needle shield 1.1 in the first position I.

The needle shield 1.1 comprises two locking catches 1.1.1 as locking means L that protrude radial outwards into a first recess 1.2.1. The first recess 1.2.1 is formed into the substantially cylindrical support body 1.2. The locking catch 1.1.1 engages the first recess 1.2.1 to retain the needle shield 1.1 in the extended first position I. The locking catch 1.1.1 comprises a skewed side 1.1.1.1 to allow the needle shield 1.1 to be slid relative to the support body 1.2 in a proximal direction towards a retracted second position II, wherein a distal movement of the needle shield 1.1 relative to the support body 1.2 is prevented.

The hollow outer body 1.3 comprises an open distal and a closed proximal end. The support body 1.2 is inserted into the open distal end of the outer body 1.3. The outer body 1.3 is movable relative to the support body 1.2 in a sliding motion in a distal direction to perform the injection stroke, whereby the outer body 1.3 slides over the support body 1.2 and the closed proximal end of the outer body 1.3 abuts a piston rod 2.4 to move a piston 2.5 connected to the piston rod 2.4. The piston 2.5 fluid-tightly seals a proximal end of an inner cavity 2.3.1 containing a medication, so that the medication is expelled through the hypodermic needle 2.1 by the distal movement of the piston 2.5.

Alternatively, the piston rod 2.4 is integrated to the outer body 1.3.

Additionally, the support body 1.2 and the outer body 1.3 may comprise means to prevent a relative rotation, so that the outer body 1.3 slides with respect to the support body 1.2 in a linear translatory motion. In particular, the means to prevent the rotation may comprise a radial projection connected to one of the outer body 1.3 or the support body 1.2. The radial projection may engage a longitudinal recess formed into a surface of the other of the outer body 1.3 or the support body 1.2.

Figure 3:
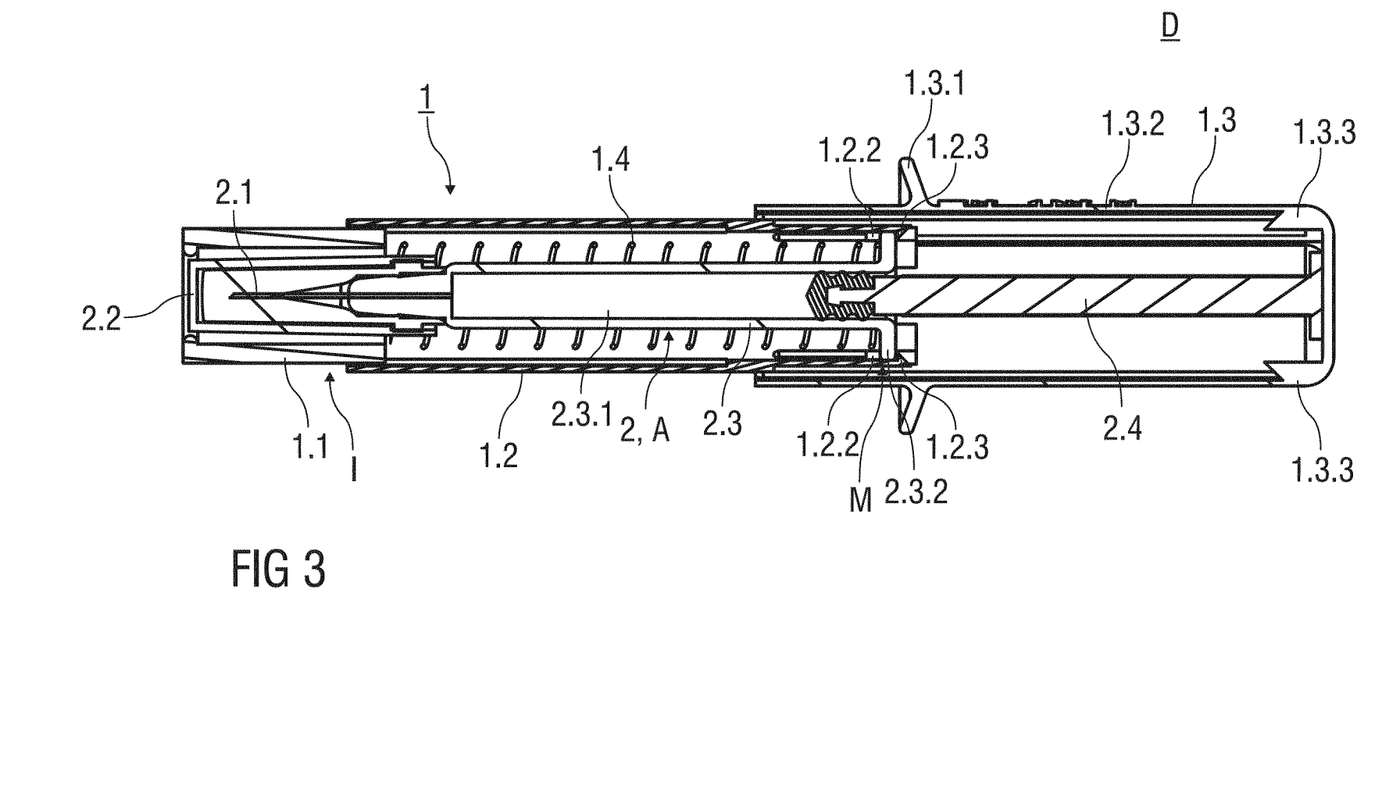
FIG. 3 shows a sectional view of the injection device according to a second cross-section prior to use.

As best seen in FIG. 3, a non-energized or only slightly energized spring means 1.4 is arranged in the support body 1.2. The spring means 1.4 bears against the needle shield 1.1 in the distal direction and against a collar 2.3.2 formed to a proximal end of the barrel 2.3 in the proximal direction. The collar 2.3.2 of the barrel 2.3 abuts two opposing and radial inwardly protruding bosses 1.2.2 formed into an inner surface of the support body 1.2 to prevent a distal displacement of the pre-filled syringe 2.3 with respect to the support body 1.2.

The spring means 1.4 may comprise a conventional compression spring made from a metal. Alternatively, the spring means 1.4 may be made from a resilient plastics material like, for example, a polymer or an elastomer.

A mounting means M of the safety device 1 comprises two clamp arms 1.2.3 located at a proximal end of the support body 1.2. The clamp arm 1.2.3 clamps to the collar 2.3 to releasably mount the pre-filled syringe 2 within the support body 1.2. According to a first embodiment of the invention, two opposing release catches 1.3.3 are moulded into an inner surface of the outer body 1.3 close to its proximal end to catch and release the clamp arms 1.2.3 mounting the pre-filled syringe 2 in the support body 1.2 at the end of the injection stroke.

Figure 4:
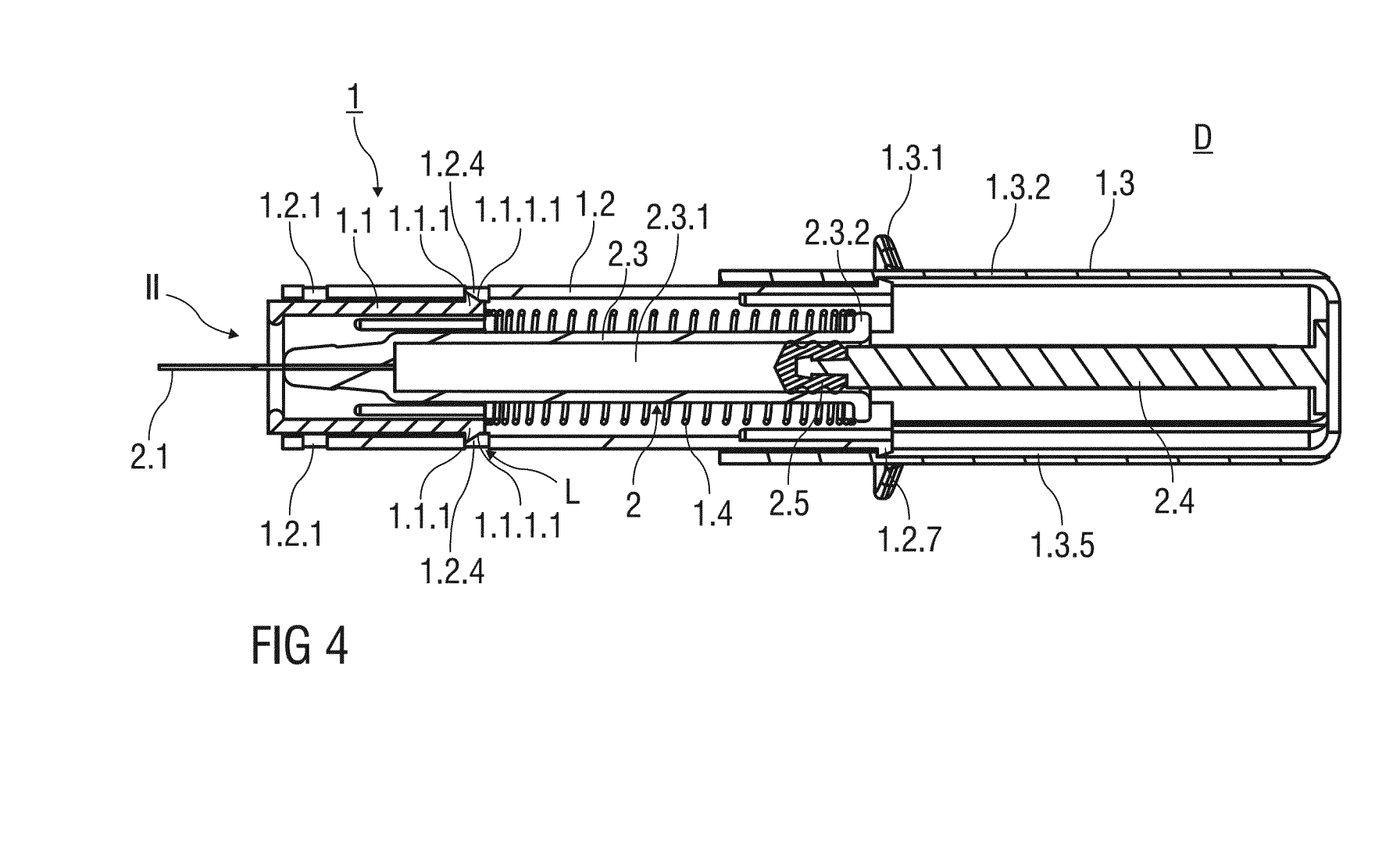
FIG. 4 shows a sectional view of the injection device with a needle shield retained in a second position.

FIG. 4 shows a sectional view of the injection device D at the beginning of the injection stroke according to the first cross-section. The needle shield 1.1 is received within the support body 1.2 in the second position II. The spring means 1.4 is compressed and fully energized. The needle cap 2.2 is removed to uncover the hypodermic needle 2.1. The fully energized spring means 1.4 biases the needle shield 1.1 and the support body 1.2 away from each other, whereby a distal movement of the needle shield 1.1 is prevented by the locking catch 1.1.1 latching to a second recess 1.2.4 of the locking means L. The second recess 1.2.4 is formed into the substantially cylindrical support body 1.2. The locking catch 1.1.1 latching to the second recess 1.2.4 irreversibly locks the needle shield 1.1 in the second position II.

FIG. 4 shows the needle shield 1.1 in the second position II, wherein the needle shield 1.1 is substantially received within the support body 1.2. In an alternative embodiment of the invention, the needle shield 1.1 is dimensioned in manner, so that the distal end of the support body 1.1 may be inserted in the proximal end of the needle shield 1.1. Respectively, the needle shield 1.1 slides over the support body 1.2 from the first position I to the second position II.

Figure 5:
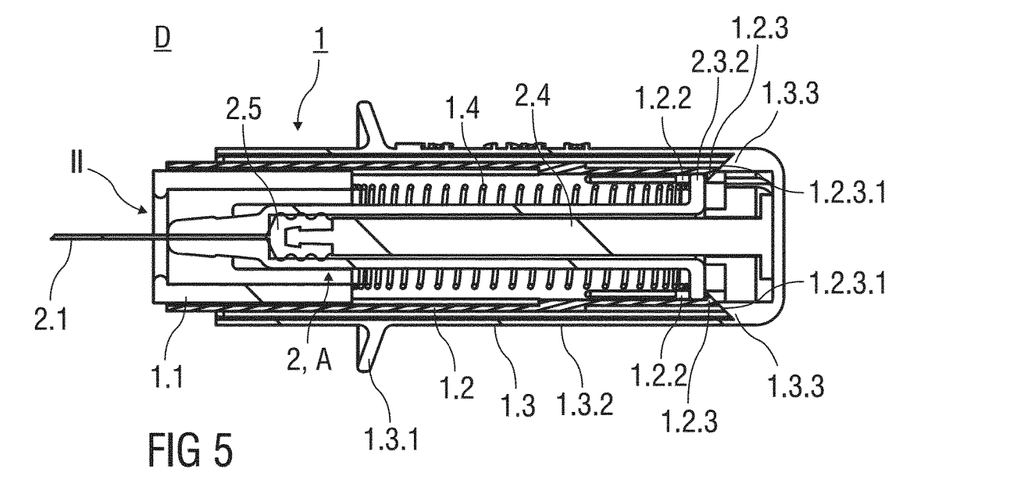
FIG. 5 shows a sectional view of the injection device at the end of an injection stroke.

As can be seen in the sectional view of FIG. 5, the support body 1.2 is received in the outer body 1.3 at the end of the injection stroke. According to the first embodiment of the invention, the clamp arm 1.2.3 comprises a tapered flank 1.2.3.1 that is located adjacent to the corresponding release catch 1.3.3 to release the clamp arms 1.2.3 mounting the pre-filled syringe 2 in the support body 1.2.

Figure 6:
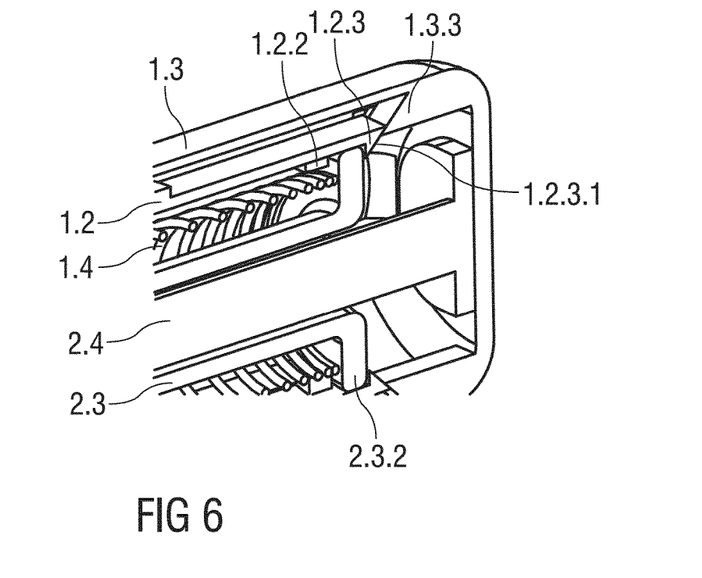
FIG. 6 shows details of a releasable mounting means of the safety device according to a first embodiment of the invention.

FIG. 6 shows the mounting means M according to the first embodiment of the invention in more detail. The tapered flank 1.2.3.1 of the clamp arm 1.2.3 engages the release catch 1.3.3, so that a further linear movement of the outer body 1.3 in the distal direction deflects the clamp arm 1.2.3 in a radial outward direction, whereby the mounting means M mounting the pre-filled syringe 2 with respect to the support body 1.2 is released.

Figure 7:
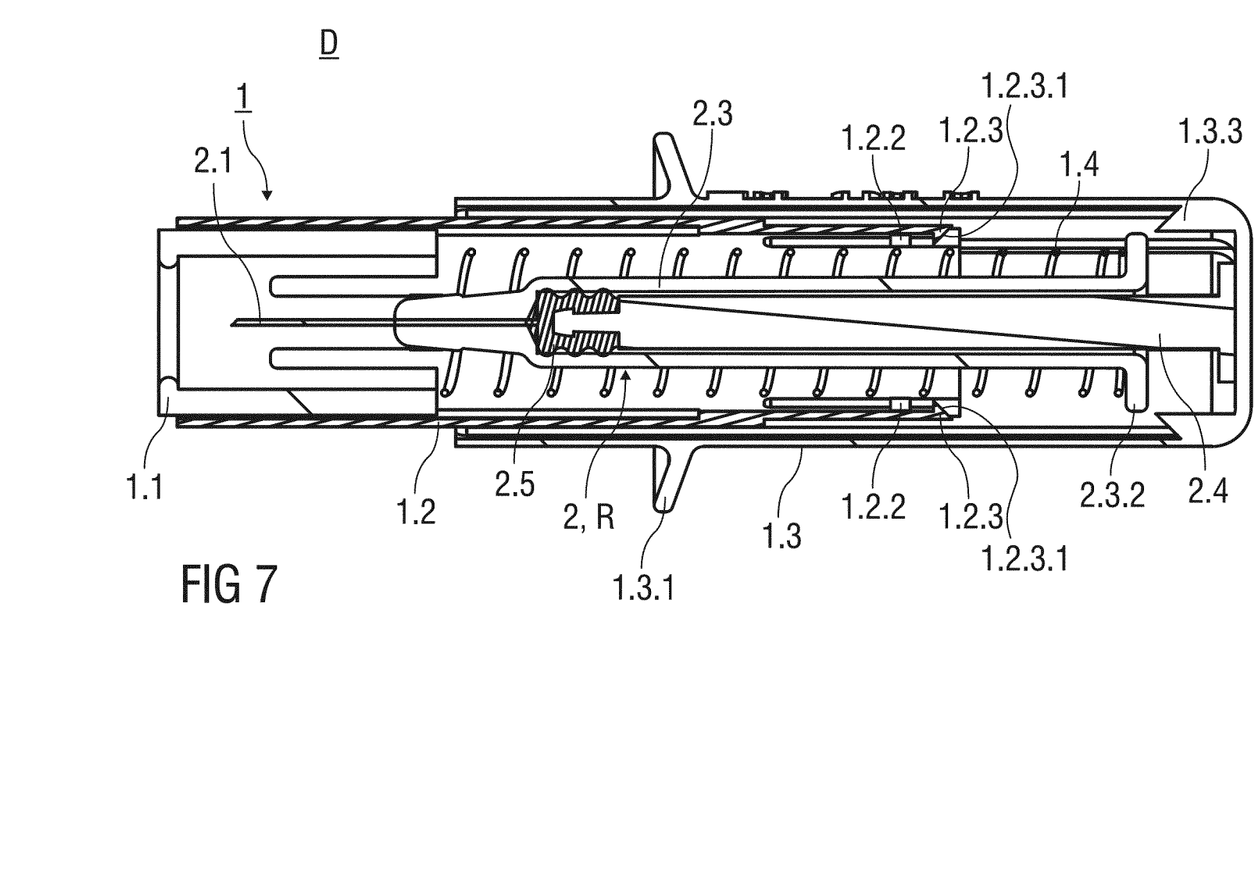
FIG. 7 shows a sectional view of an injection device with a pre-filled syringe in a retracted position.

As illustrated in FIG. 7 the spring means 1.4 bearing against the collar 2.3.2 relaxes and moves the pre-filled syringe 2 proximally relative to the support body 1.2 to a retracted position R. As the piston rod 2.4 abuts the closed proximal end of the outer body 1.3, the outer body 1.3 jointly moves with the pre-filled syringe 2 in the proximal direction, so that the pre-filled syringe is retained within the support body 1.2 and within the outer body 1.3 in the retracted position R.

Figure 8:
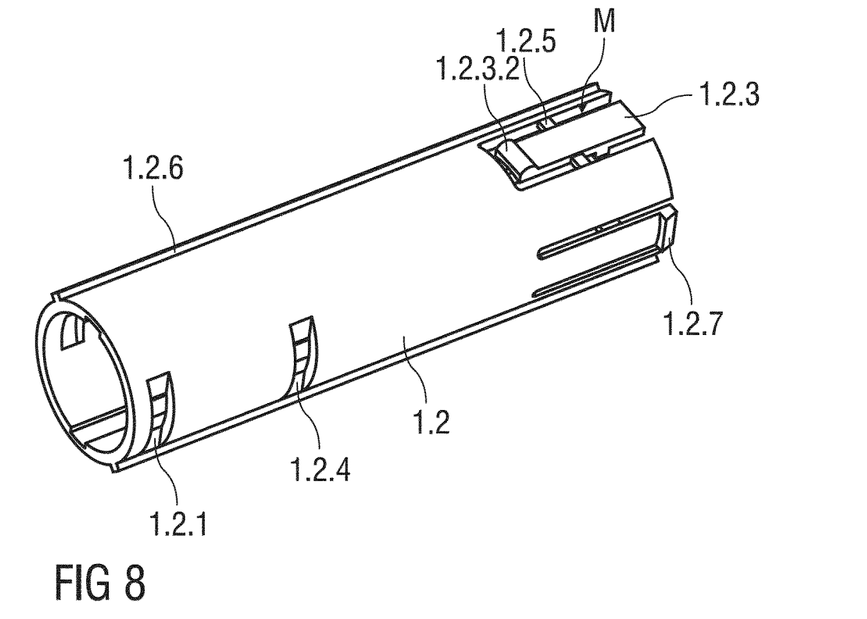
FIG. 8 shows a support body of a safety device according to a second embodiment of the invention in a perspective view.
Figure 9:
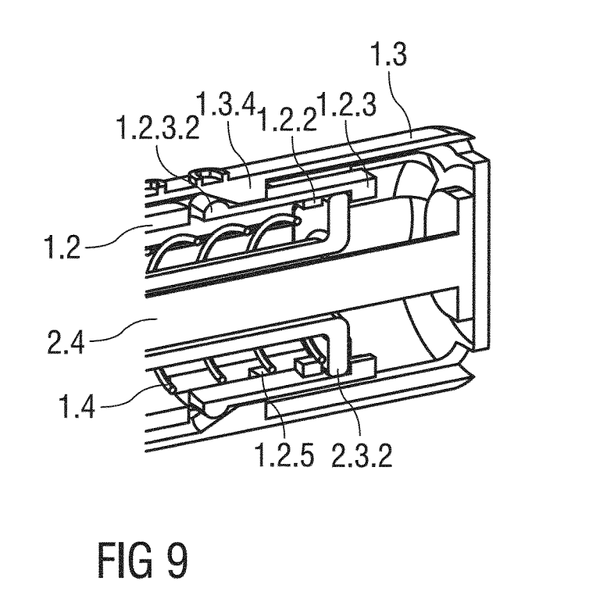
FIG. 9 shows details of a releasable mounting means of the safety device according to the second embodiment of the invention.

FIGS. 8 and 9 show the mounting means M according to a second embodiment of the invention.

FIG. 8 shows a support body 1.2 of a safety device 1 according to a second embodiment of the invention in a perspective view. The clamp arm 1.2.3 is hinged to the support body 1.2 and arranged so as to allow for a pivoting movement of the clamp arm 1.2.3 about a hinge 1.2.5 to release the mounting means M.

A longitudinal rib 1.2.6 extends over a substantial axial length of the support body 1.2 that is received in a corresponding notch (not illustrated) formed into an inner surface of the outer body 1.3. When the outer body 1.3 is axially translated with respect to the support body 1.2 in the distal direction during the injection, the longitudinal rib travels along the notch to prevent a relative rotation between the outer body 1.3 and the support body 1.2.

A limiter stop 1.2.7 is formed to the proximal end of the support body 1.2 that is arranged to limit the axial displacement of the support body 1.2 with respect to the outer body 1.3. During the injection, the limiter stop 1.2.7 travels along a correspondingly shaped longitudinal recess 1.3.5 best illustrated in FIGS. 2 and 4 to prevent a relative rotation of the support body 1.2 and the outer body 1.3. The limiter stop 1.2.7 abuts against a distal end of the longitudinal recess 1.3.5 to limit the axial displacement of the support body 1.2 with respect to the outer body 1.3 in the distal direction.

FIG. 9 shows details of a releasable mounting means M of the safety device 1 according to the second embodiment of the invention. The mounting means M according to the second embodiment comprises the clamp arm 1.2.3 connected to the support body 1.2 via the hinge 1.2.5. The clamp arm 1.2.3 initially latches to the collar 2.3.2 of the barrel 2.3. An inward projection 1.3.4 is formed to an inner surface of the outer body 1.3. The inward projection 1.3.2 is arranged to abut against the outward projection 1.2.3.2 of the clamp arm 1.2.3 hinged to the support body 1.2 to release the mounting means M that mounts the pre-filled syringe 2 to the support body 1.2.

The injection is carried out in stages. In a first stage, the hypodermic needle 2.1 is inserted into the skin of the patient. The needle shield 1.1 is moved with respect to the support body 1.2 from the first position I in the proximal direction against the biasing force of the spring means 1.4 towards the second position II.

As indicated in FIG. 4, the spring means 1.4 is compressed and fully energized when the needle shield 1.1 reaches the second position II. The locking catch 1.1.1 latches to the second recess 1.2.4 to lock the needle shield 1.1 in the second position II. The latching of the locking catch 1.1.1 may produce a first audible feedback indicating that the spring means 1.4 is charged and the safety features retracting the pre-filled syringe 2 after the injection are activated.

The needle shield 1.1 may be moved in the proximal direction by orientating the substantially cylindrical safety device 1 essentially perpendicular to the skin surface and pushing the safety device 1 towards the skin surface, whereby the needle shield 1.1 moves from the first position I to the second position II and the hypodermic needle 2.1 pierces the skin surface of the patient.

After the hypodermic needle 2.1 is inserted, the medication or drug contained in the inner cavity 2.3.1 is expelled through the hypodermic needle 2.1 in the second stage of the injection. The outer body 1.3 is moved in the distal direction to perform the injection stroke, whereby the piston rod 2.4 connected to the piston 2.5 is pushed distally and the medication is disposed beneath the skin of the patient.

According to the first embodiment of the invention, the tapered flank 1.2.3.1 of the clamp arm 1.2.3 engages the release catch 1.3.3 at the end of the injection stroke, as shown in FIG. 5. The clamp arms 1.2.3 are splayed releasing the mounting means M mounting the pre-filled syringe 2 within the support body 1.2.

According to the second embodiment of the invention, the outward projection 1.2.3.2 of the clamp arm 1.2.3 hinged to the support body 1.2 abuts against the inward projection 1.3.4 at the end of the injection stroke. The outward projection is depressed radially inwards, whereupon the clamp arm 1.2.3 pivots about the hinge 1.2.5 releasing the mounting means M.

The collar 2.3.2 of the pre-filled syringe 2 disengages the clamp arm 1.2.3 whereby a second audible feedback is produced. The second audible feedback informs the user carrying out the injection that the injection device D may be removed from the injection site. As soon as the injection device D is taken away, the spring means 1.4 relaxes and pushes the pre-filled syringe 2 in the proximal direction towards a retracted position R indicated in FIG. 7. In the retracted position R, the pre-filled syringe 2 is completely retained inside the safety device 1. The hypodermic needle 2.1 is surrounded by the support body 1.2 and a proximal section of the pre-filled syringe 2 is retained within the hollow outer body 1.3. A re-exposure of the hypodermic needle 2.1 is prevented by the spring means 1.4 biasing the pre-filled syringe 2 in the proximal direction.

The support body 1.2 is at least partially received within the outer body 1.3 after the injection has been carried out and the pre-filled syringe 2 is in the retracted position R. The outer body 1.3 may comprise additional limiting means (not shown) that limit a proximal movement of the outer body 1.3 with respect to the support body 1.2 after the injection stroke has been carried out. The outer body 1.3 may be dimensioned to cover the second recess 1.2.4, so that the locking catch 1.1.1 interacting with the second recess 1.2.4 is inaccessible from outside. This may prevent a person from tampering with the locking means L to unlock the needle shield 1.1, so that a re-use of the safety device 1 is prevented.

The invention claimed is:

1. A safety device for a pre-filled syringe, comprising:
    a hollow support body for retaining the pre-filled syringe,
    a hollow needle shield movable relative to the support body from a first position to a second position,
    a releasable mounting member to mount the pre-filled syringe within the support body,
    an outer body slidably arranged relative to the support body, wherein, at an end of an injection stroke, the outer body releases the releasable mounting member and substantially receives the support body,
    a locking mechanism configured to inhibit movement of the needle shield to the first position when the needle shield is in the second position, the locking mechanism comprising
        at least one locking catch configured to protrude from the needle shield into a first recess formed into the support body to retain the needle shield in the first position, and
        a second recess formed into the support body, wherein the at least one locking catch is configured to latch to the second recess to irreversibly lock the needle shield in the second position after the needle shield moves from the first position to the second position, and
    a spring arranged within the support body in a non-energized or partially energized state, wherein movement of the needle shield from the first position to the second position fully energizes the spring.

2. The safety device according claim 1, wherein the movement of the needle shield from the first position to the second position causes the safety device to generate an audible feedback indicating that the spring is fully energized.

3. The safety device according to claim 1, wherein the spring is made from plastics material.

4. The safety device according to claim 1, wherein, when the outer body releases the releasable mounting member, the safety device generates an audible feedback.

5. The safety device according to claim 1, wherein the releasable mounting member comprises at least one clamp arm connected or integrated to the support body and adapted to clamp to a collar of the pre-filled syringe.

6. The safety device according to claim 5, wherein the outer body comprises a release catch that engages a tapered flank of the clamp arm to deflect the at least one clamp arm in a radial outward direction to release the releasable mounting member.

7. The safety device according to claim 5, wherein the at least one clamp arm connects to the support body at a hinge and comprises an outward projection adapted to be engaged by an inward projection formed to an inner surface of the outer body to pivot the at least one clamp arm about the hinge to release the releasable mounting member.

8. An injection device comprising:
a pre-filled syringe with a hypodermic needle; and
a safety device comprising:
  a hollow support body retaining the pre-filled syringe in an advanced position such that the hypodermic needle protrudes beyond a distal end of the support body,
  an outer body slidable relative to the support body,
  a hollow needle shield movable relative to the support body from a first position to a second position, wherein the hypodermic needle is surrounded by the needle shield in the first position and the hypodermic needle is exposed in the second position,
  a releasable mounting member mounting the pre-filled syringe within the support body the releasable mounting member comprising at least one clamp arm connected or integrated to the support body and adapted to clamp to a collar of the pre-filled syringe, wherein a release catch of the outer body is configured to engage a tapered flank of the clamp arm to deflect the at least one clamp arm in a radial outward direction to release the releasable mounting member, and
  a spring arranged within the support body in a non-energized or partially energized state, wherein movement of the needle shield from the first position to the second position energizes the spring.

9. The injection device according to claim 8, wherein the spring engages the collar of the pre-filled syringe to move the pre-filled syringe proximally with respect to the support body.

10. The injection device according to claim 8, wherein, at an end of an injection stroke, the outer body releases the releasable mounting member and the spring relaxes and moves the pre-filled syringe from the advanced position to a retracted position in which the hypodermic needle is surrounded by the support body.

11. The safety device according to claim 1, wherein, in the first position, the hollow needle shield is configured to surround a hypodermic needle of the pre-filled syringe, and in the second position, the hollow needle shield is configured to expose the hypodermic needle.

12. The safety device according to claim 1, wherein the needle shield comprises a surface adapted to rest on a skin of a patient.

13. The safety device according to claim 1, wherein the needle shield is configured to move from the first position to the second position against a biasing force of the spring, and the spring is in the non-energized or partially energized state in the first position.

14. The injection device according to claim 8, wherein the movement of the needle shield from the first position to the second position fully energizes the spring.

15. The injection device according to claim 8, wherein the needle shield is configured to move from the first position to the second position against a biasing force of the spring, and the spring is in the non-energized or partially energized state in the first position.

16. The injection device according to claim 8, wherein the needle shield comprises a surface adapted to rest on a skin of a patient.

17. The safety device according to claim 8, further comprising a locking mechanism configured to inhibit movement of the needle shield to the first position when the needle shield is in the second position, the locking mechanism comprising
  at least one locking catch configured to protrude from the needle shield into a first recess formed into the support body to retain the needle shield in the first position, and
  a second recess formed into the support body, wherein the at least one locking catch is configured to latch to the second recess to irreversibly lock the needle shield in the second position after the needle shield moves from the first position to the second position.

18. A safety device for a pre-filled syringe, comprising:
a hollow support body for retaining the pre-filled syringe,
an outer body slidable relative to the support body,
a hollow needle shield movable relative to the support body from a first position to a second position,
a releasable mounting member to mount the pre-filled syringe within the support body, the releasable mounting member comprising at least one clamp arm connected or integrated to the support body and adapted to clamp to a collar of the pre-filled syringe, and the at least one clamp arm connecting to the support body at a hinge and comprising an outward projection adapted to be engaged by an inward projection formed to an inner surface of the outer body to pivot the at least one clamp arm about the hinge to release the releasable mounting member, and
a spring arranged within the support body in a non-energized or partially energized state, wherein movement of the needle shield from the first position to the second position energizes the spring.

19. The safety device according claim 17, wherein the movement of the needle shield from the first position to the second position causes the safety device to generate an audible feedback indicating that the spring is fully energized.

20. A safety device for a pre-filled syringe, comprising:
a hollow support body for retaining the pre-filled syringe,
a hollow needle shield movable relative to the support body from a first position to a second position,
a releasable mounting member to mount the pre-filled syringe within the support body,
an outer body slidable relative to the support body,
wherein the releasable mounting member comprises at least one clamp arm connected or integrated to the support body and adapted to clamp to a collar of the pre-filled syringe,
a locking mechanism configured to inhibit movement of the needle shield to the first position when the needle shield is in the second position, the locking mechanism comprising
  at least one locking catch configured to protrude from the needle shield into a first recess formed into the support body to retain the needle shield in the first position, and
  a second recess formed into the support body, wherein the at least one locking catch is configured to latch to the second recess to irreversibly lock the needle shield in the second position after the needle shield moves from the first position to the second position, and
a spring arranged within the support body in a non-energized or partially energized state, wherein movement of the needle shield from the first position to the second position fully energizes the spring.

\* \* \* \* \*